United States Patent [19]

Bear et al.

[11] Patent Number: 4,909,911
[45] Date of Patent: Mar. 20, 1990

[54] PROCESS FOR CATALYTICALLY REDUCING DIOXYGEN USING DIRHODIUM COMPLEXES

[75] Inventors: John L. Bear; Chao-Liang Yao, both of Houston, Tex.

[73] Assignee: University of Houston, Houston, Tex.

[21] Appl. No.: 258,849

[22] Filed: Oct. 17, 1988

[51] Int. Cl.[4] .......................... B25B 1/30; C25B 9/00
[52] U.S. Cl. ...................................... 204/84; 204/129; 204/294; 502/166; 502/168
[58] Field of Search ............... 204/84, 129, 242, 291, 204/294, 290 R; 502/166, 168, 171; 556/137, 136; 546/6; 549/3, 13

[56] References Cited

U.S. PATENT DOCUMENTS 4,451,270 5/1984 Roman et al. ........................... 55/38
4,652,647 3/1987 Schlosberg et al. ................. 502/168

OTHER PUBLICATIONS

S. E. Creager and R. W. Murray, "Electrochemical Reactivity of Manganese (II) Porphyrins, Effects of Dioxygen, Benzoic Anhydride, and Axial Ligands," 26, Inorg. Chem., 2612 (1987).
J. L. Bear, L. N. Liu and K. M. Kadish, "Structural, ESR, and Electrochemical Properties of Two[Rh$_2$(Ap)$_4$]$^+$ Geometric Isomers (ap=2-Anilinopyridinate), A True Mixed-Valent Rhodium (III) Complex," 26, Inorganic Chem., 2927-9 (1987).
E. S. Takeuchi and R. W. Murray, "Metalloporphyrin Containing Carbon Paste Electrodes," 188, J. Electroanal. Chem., 49-57 (1985).
D. A. Tocher and J. H. Tocher, "Synthesis and Spectro-electrochemical Characterization of a Novel Rhodium (II) Dimer, Rh$_2$(phNpy)$_4$", 104, Inorganica Chimica Acta, L15-L17 (1985).
Calabrese et al., (1983), J. Am. Chem. Soc., 105:5594–5600.

Primary Examiner—John F. Niebling
Assistant Examiner—Kathryn Gorgos
Attorney, Agent, or Firm—Arnold, White & Durkee

[57] ABSTRACT

Dirhodium complexes such as tetrakis(μ-2-anilinopyridinato)dirhodium are used in the catalytic reduction of dioxygen. An electric potential is applied to the dirhodium complex either dissolved in solution or supported by an electrode.

13 Claims, 2 Drawing Sheets

PROCESS FOR CATALYTICALLY REDUCING DIOXYGEN USING DIRHODIUM COMPLEXES

BACKGROUND OF THE INVENTION

The present invention relates to processes and compositions for reducing dioxygen. More particularly, the present invention relates to a catalytic process using dirhodium complexes to reduce dioxygen.

Extensive efforts have gone into finding efficient catalysts that can promote the reaction of dioxygen with oxidizable substrates. Biological catalysts are effective in activation and transport of dioxygen. Accordingly, substantial work has been done with metalloporphyrin catalysts. However, there are few additional examples of transition-metal complexes that have the desired properties and reactivity to be utilized in the catalytic activation of dioxygen.

Activation of molecular oxygen by transition-metal complexes can occur by way of a one-electron-transfer process, a two-electron-transfer process, or a four-electron-transfer process which generate the superoxide ion, peroxide ion, or oxide ion in aprotic media. The superoxide ion, $O_2^-$, is reactive towards some organic substrates either by nucleophilic substitution or by direct oxidation. Superoxide ions have been used for the degradation of chloroalkanes, chloroalkenes, and polychloro aromatic hydrocarbons. Solutions containing $O_2^-$ can be prepared in aprotic solvents by electrochemical methods or by solublizing $KO_2$ with 18-crown-6-ether. However, there is still a need to find convenient and inexpensive pathways to generate $O_2^-$.

A catalytic cycle involving manganese porphyrins for the reduction of dioxygen has been reported by S. E. Creager and R. W. Murray, "Electrochemical Reactivity of Manganese (II) Porphyrins. Effect of Dioxygen, Benzoic Anhydride, and Axial Ligands," 26 Inorg. Chem. 2612, (1987). Mixtures of the porphyrin and benzoic anhydride lead to a reduction of dioxygen at a control potential of $-0.40$ V vs SCE. This process involved reduction by more than two electrons and heterolysis of the O—O bond by benzoic anhydride. However, the manganese porphyrin complex did not show catalytic behavior in the absence of benzoic anhydride.

Accordingly, it would be a significant advancement in the art to provide a catalyst and process for the continuous generation of superoxide ion. Such a catalyst and process are disclosed and claimed herein.

BRIEF SUMMARY OF THE INVENTION

The present invention is directed to an apparatus and process for the catalytic reduction of dioxygen utilizing dirhodium complexes. In a preferred embodiment, tetrakis ($\mu$-2-anilinopyridinato)dirhodium is utilized to reduce dioxygen to form superoxide complexes. The superoxide ion can then be used in the formation of hydrogen peroxide or for the degradation of various organic substrates such as chloroalkanes, chloroalkenes, and polychloro aromatic hydrocarbons.

The preferred embodiment utilizes the isomer in which the four pyridine nitrogens of the anilinopyridine ligands are bound to one rhodium ion and the four anilino nitrogens of the bridging ligands are bound to the second rhodium ion. The complex can be reduced in $CH_2Cl_2$ in the presence of molecular oxygen; this will result in the formation of $(ap)_4Rh^{II}Rh^{III}(O_2^-)$ where (ap) = 2-anilinopyridinate ion. Further reduction at $-0.48$ V gives the superoxide complex, $[(ap)_4Rh^{II}_2(O_2^-)]^-$.

In a second preferred embodiment, each rhodium is equatorially bound by two pyridine nitrogens and two anilino nitrogens trans to their own kind.

In additional preferred embodiments, dirhodium is bound to four 2-amino-4-methylpyridinate, 2-aminopyridinate, 5-chloro-2-aminopyridinate or 3,5-dichloro-2-aminopyridinate ligands through two amino and two pyridyl nitrogen donors in a cis arrangement.

The dirhodium complexes of the present invention can be applied to an electrode such as a carbon paste electrode so that the reduction of dioxygen can take place in an aqueous solution. The application of $-0.48$ V in the presence of molecular oxygen and water results in the formation of hydrogen peroxide.

DETAILED DESCRIPTION OF THE PREFERRED EMBODIMENTS

Tetrakis($\mu$-2-anilinopyridinato)dirhodium(II,III) cation, $[(ap)_4Rh^{II}Rh^{III}]^+$, has four possible geometric isomers. Two of those isomers were synthesized and identified previously. J. L. Bear, L. M. Liu, and K. M. Kadish, "Structural, ESR, and Electrochemical Properties of Two $[Rh_2(ap)_4]^+$ Geometric Isomers (ap=2-Anilinopyridinate). A True Mixed-Valent Rhodium-(II)-Rhodium(III) Complex," 26 Inorganic Chem. 2927-9 (1987). The teachings of the article are herein incorporated by reference.

Figure 1:
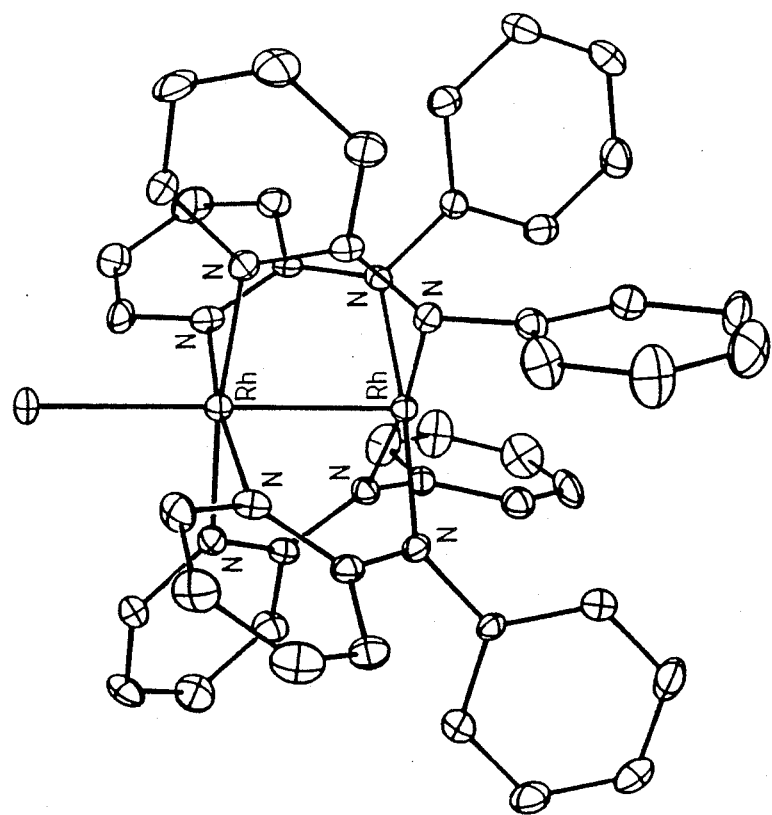
FIG. 1 is a schematic illustration of the structure of the preferred embodiment of a dirhodium complex of the present invention.

The molecular structure of $(ap)_4Rh^{II}Rh^{III}Cl$ is shown in FIG. 1. This complex is the most polar of the four possible geometric isomers that could be formed by the 2-anilinopyridinate bridging ligand. Each of the rhodium ions is in a different equatorial ligand environment, and in addition, only one axial ligand bond is formed. This is true for either of the two formal oxidation states, $(ap)_4RH^{II}_2$ or $[(ap)_4Rh^{II}Rh^{III}]^+$. The chloride ion is bound to the rhodium with four pyridine nitrogen bonds, and this rhodium is probably the preferred binding site of dioxygen in the complexes to be discussed. The ESR spectrum of $(ap)_4Rh^{II}Rh^{III}Cl$ is unique among all other dirhodium complexes in that the odd electron is localized on one rhodium ion, showing the complex to contain a true Rh(II)–Rh(III) dimer unit.

The $(ap)_4Rh_2Cl$ was synthesized by heating 300 mg of $Rh_2(OAc)_4$ in 5 g of 2-anilinopyridine under vacuum at 130 °C. for 24 h. Unreacted 2-anilinopyridine was removed by sublimation, and the solid mixture was then dissolved in a $CH_2Cl_2$ solution containing $CCl_4$. Repeated purification on a silica gel column with 5% $CH_3OH$ in $CH_2Cl_2$ gave a pure product in 40% yield.

The $(ap)_4Rh_2ClO_4$ was generated by reducing 50 mg of $(ap)_4Rh_2Cl$ in $CH_2Cl_2$, 0.05 M TBAP at $-0.65$ V vs.

SCE under a CO atmosphere. The pinkish brown (ap)$_4$Rh$_2$(CO) product precipitates from solution. This precipitate was filtered and washed with cold CH$_2$Cl$_2$. Carbon monoxide was removed, and (ap)$_4$Rh$_2$ClO$_4$ was generated by oxidizing the CO adduct at +0.2 V in CH$_2$Cl$_2$, 0.1 M TBAP under an argon atmosphere. All electric potentials were measured versus a saturated calomel electrode.

All reagents for synthesis were used as received. Spectroscopic grade CH$_2$Cl$_2$ was purified by distillation from CaH$_2$ under N$_2$. Dimethylformamide (DMF) was vacuum-distilled from 4-A activated molecular sieves, and tetrahydrofuran (THF) was distilled from CaH$_2$ followed by distillation over Na/benzophenone under N$_2$. The supporting electrolyte, tetra-n-butylammonium perchlorate (TBAP), was twice recrystallized from ethanol and dried in a vacuum oven at 40 °C. Ultrahigh-purity O$_2$ (Big Three, Inc.) with a maximum of 3 ppm of H$_2$O was used.

The (ap)$_4$Rh$_2$Cl undergoes a single reversible reduction at $E_{\frac{1}{2}} = -0.38$ V and a single reversible oxidation at $E_{\frac{1}{2}} = +0.52$ V in CH$_2$Cl$_2$, 0.1 M TBAP. The bound Cl$^-$ ion on (ap)$_4$Rh$_2$Cl can be replaced by ClO$_4^-$ to give (ap)$_4$Rh$_2$ClO$_4$ and this leads to a 70-mV shift in the reduction potential and a 10-mV shift in the oxidation potential. (ap)$_4$Rh$^{II}_2$ is formed upon reduction at $E_{\frac{1}{2}} = -0.31$ V (process 1), while [(ap)$_4$Rh$^{II}_2$]$^{2+}$ is generated upon oxidation at $E_{\frac{1}{2}} = 0.53$ V (process 2).

The potentials for processes 1 and 2 do not change when oxygen is bubbled through the solution, but under these conditions, a new quasi-reversible reduction (process 3) appears at $E_{\frac{1}{2}} = 0.48$ V. The ratio of cathodic peak currents for process 3 to those for process 2 decreases with either an increase in scan rate or a decrease in temperature. This clearly indicates a reaction of electrogenerated (ap)$_4$Rh$^{II}_2$ with dioxygen.

The electrochemistry of (ap)$_4$Rh$_2$ClO$_4$ at a rotating Pt-disk electrode in the presence of O$_2$ gives results similar to those obtained by cyclic voltammetry. In the absence of dioxygen, the complex undergoes a one-electron reduction and a one-electron oxidation. However, in the presence of dioxygen, there are two one-electron reductions; the latter of which occurs at $E_{\frac{1}{2}} = 0.48$ V. There is no interference from the direct reduction of O$_2$, which occurs at $E_p = -1.0$ V in CH$_2$Cl$_2$, 0.1 M TBAP at a scan rate of 0.10 V/s.

The ratio of the limiting current for process 3 to that for process 2 by rotating-disk voltammetry is 0.72 at 500 rpm, and the data thus suggest the following sequence of reactions:

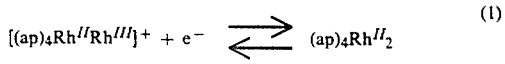  (1)

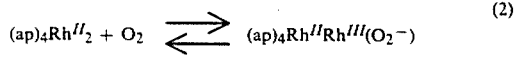  (2)

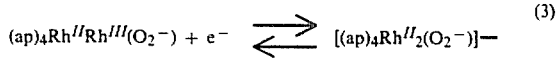  (3)

The ultimate product of the first reduction (2) is a dirhodium dioxygen adduct and is assigned as the rhodium-superoxide complex, (ap)$_4$Rh$^{II}$Rh$^{III}$(O$_2^-$), on the basis of its UV-visible spectrum, which clearly indicates the presence of a Rh$^{II}$Rh$^{III}$ center.

Controlled-potential electrolysis of (ap)$_4$Rh$^{II}$Rh$^{III}$(O$_2^-$) was carried out in CH$_2$Cl$_2$ under N$_2$ at −0.60 V, and the integrated current-time curve gave a total of 1.0 ±0.1 electrons transferred as the current decreased to zero. However, the residual current was larger when electrolysis of the same solution was carried out under an O$_2$ atmosphere. Under these conditions, the steady-state current did not decay to zero after 5 h of electrolysis, thus, indicating that no significant decomposition of the complex occurred. The final steadystate current also did not vary with changes in the partial pressure of oxygen between 160 and 760 mmHg, suggesting that the reaction between (ap)$_4$Rh$^{II}_2$ and O$_2$ is pseudo first order with respect to the dirhodium complex. Finally, a turnover number of 4 was calculated when the bulk electrolysis of (ap)$_4$Rh$^{II}$Rh$^{III}$(O$_2^-$) was stopped after 1 h.

The above electrochemical results support a catalytic reduction of dioxygen in the sense that the original irreversible reduction of O$_2$ is shifted from $E_p = -1.0$ V in CH$_2$Cl$_2$ containing 0.1 M TBAP to $E_{\frac{1}{2}} = -0.48$ V in the same solution containing [(ap)$_4$Rh$^{II}$Rh$^{III}$]$^+$. The reduction of (ap)$_4$Rh$^{II}$Rh$^{III}$(O$_2^-$) occurs at the Rh$^{II}$Rh$^{III}$ center and results in the overall EC catalytic process shown in FIG. 4.

Figure 4:
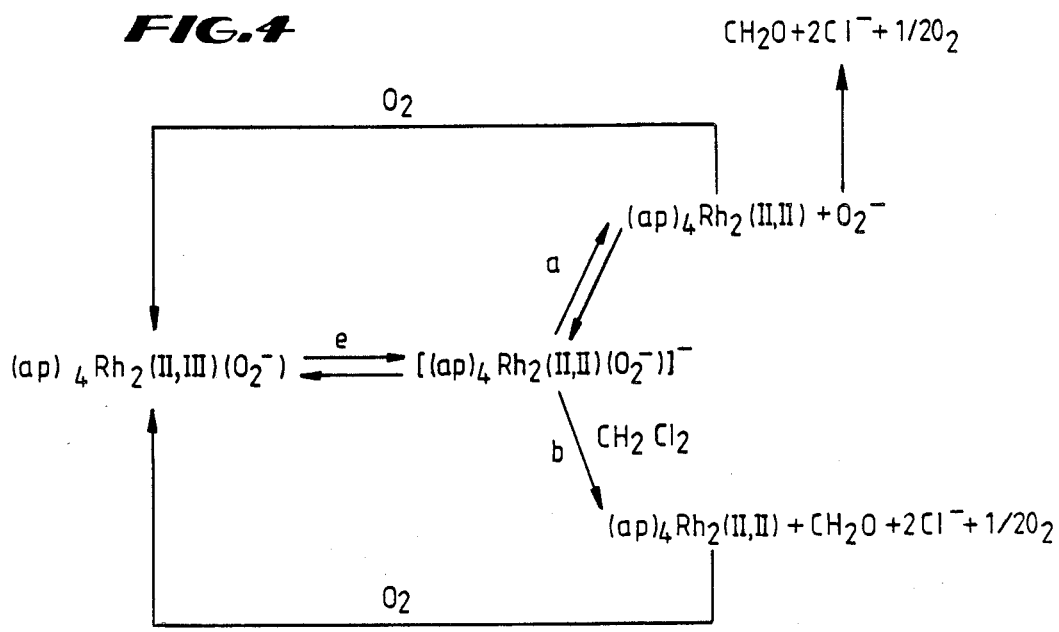
FIG. 4 is a scheme of the reaction mechanism of $(ap)_4Rh_2(O_2^-)$ under $O_2$ in $CH_2Cl_2$.

Route a in FIG. 4 involves an association-dissociation mechanism. [(ap)$_4$Rh$^{II}_2$(O$_2^-$)]$^-$ undergoes dissociation of O$_2$ to regenerate (ap)$_4$Rh$^{II}$Rh$^{III}$(O$_2^-$). The superoxide ion is known to react with CH$_2$Cl$_2$ and gives as final products CH$_2$O, Cl$^-$, and O$_2$, and this reaction most likely occurs since no free O$_2$ was detected by ESR in CH$_2$Cl$_2$. The second process in FIG. 4 (route b) involved the direct attack of [(ap)$_4$Rh$^{II}_2$(O$_2^-$)]$^-$ by a CH$_2$Cl$_2$ solvent molecule, and this will also regenerate (ap)$_4$Rh$^{II}$Rh$^{III}$(O$_2^-$) under an O$_2$ atmosphere. Both processes a and b provide the necessary thermodynamic driving force to shift the reduction potential of O$_2$ through the electrode reduction of dirhodium oxygen adducts. The data obtained can be used to explain either process a or process b, and neither of the two possible routes can be eliminated. However, if route b occurs, the rate of the reaction of [(ap)$_4$Rh$^{II}_2$(O$_2^-$)]$^-$ CH$_2$Cl$_2$ must be slow, since an ESR spectrum of this species is easily obtained in this solvent.

Figure 2:
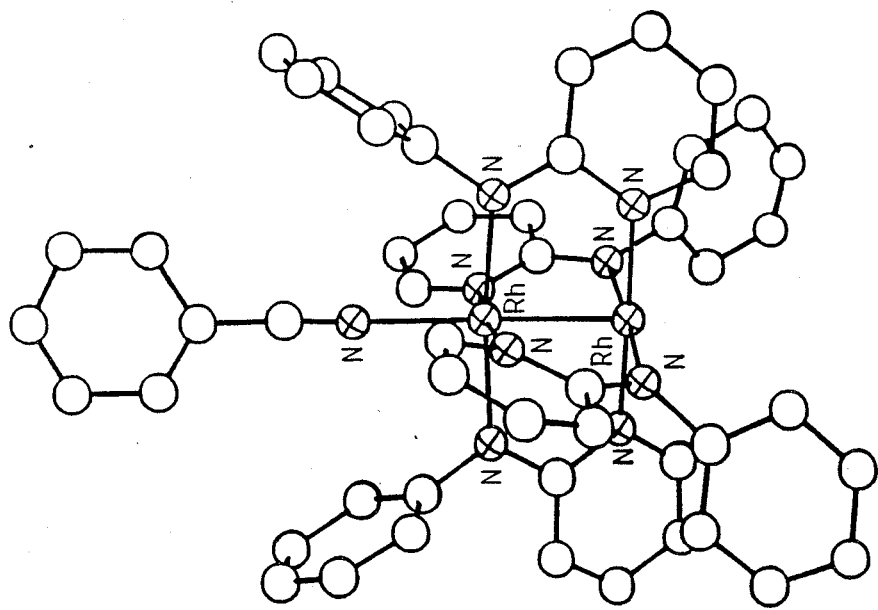
FIG. 2 is a schematic illustration of the structure of a second embodiment of a dirhodium complex of the present invention.

In a second preferred embodiment, each rhodium in the dirhodium complex is equatorially bound by two pyridine nitrogens and two anilino nitrogens trans to their own kind. Such a compound is illustrated in FIG. 2 which depicts a dirhodium(II) ion bridged by four 2-anilinopyridinate ions and one axial benzonitrile ligand.

Figure 3:
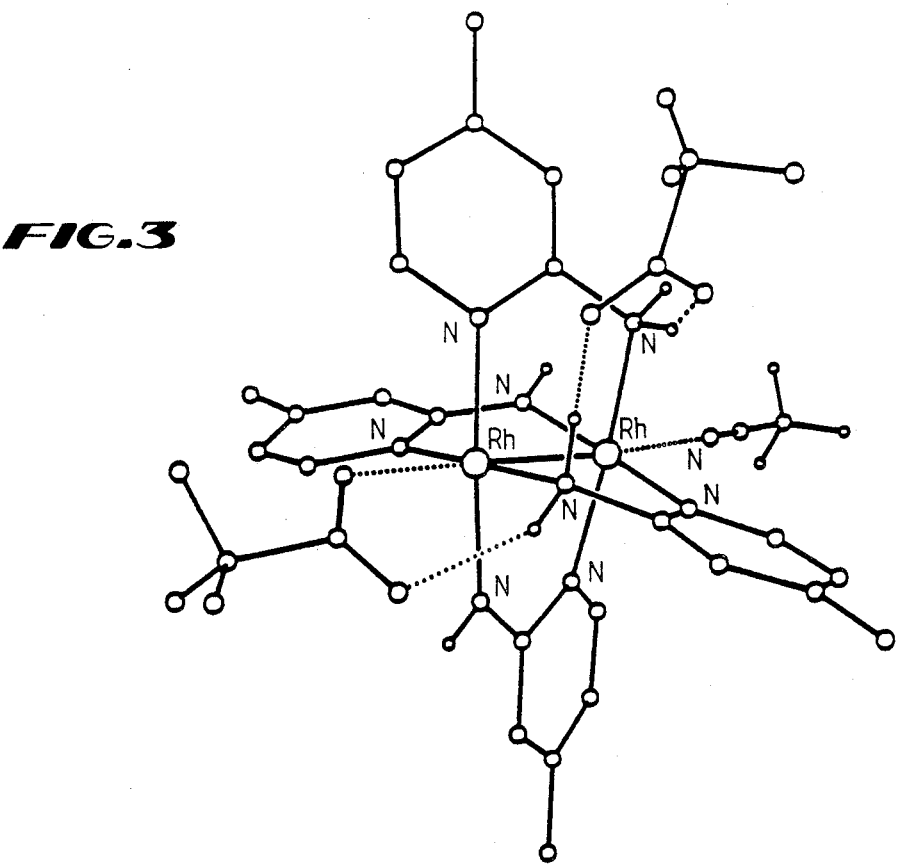
FIG. 3 is a schematic illustration of the structure of a third embodiment of a dirhodium complex of the present invention.

FIG. 3 illustrates still another embodiment of the present invention comprising Bis($\mu$-2-paramethylaminopyridine)bis($\mu$-2-paramethylaminopyridinato)dirhodium(II) trifluoroacetate.

Other dirhodium complexes also form part of the present invention. The complexes can be represented by the formula Rh$_2$(L)$_4$ where L is a bridging ligand containing two donor atoms selected from the group consisting of N, S, P and O and combinations thereof provided that no more than one of the donor atoms in each ligand is O. Suitable ligands include amides, thioamides, amidines, and 2-aminopyridines. Substituted derivatives of these compounds can also be used.

Each rhodium atom in the dirhodium complexes of this invention is in a formal +1, +2 or +3 oxidation state. The final step in the activation (reduction) of dioxygen occurs at the rhodium centers through electron transfer from rhodium to O$_2$. The redox potential for this electron transfer process is controlled by the electron pair donor-acceptor ability of the four bridging ligands. preferably, the redox potential is within the range of +0.3V to −0.5V. Accordingly, other bridging ligands with similar donor-acceptor abilities of the bridging ligands of the preferred embodiments can be used in dirhodium complexes to achieve the desired catalytic properties.

The dirhodium catalysts can also be used to activate dioxygen in aqueous solutions. However, it is necessary to disburse the water insoluble dirhodium catalysts in a working electrode material. A suitable electrode can be made from carbon paste. The most common preparation of paste electrodes is by hand mixing graphite powder and Nujol in a 5 g/3 mL ratio in a mortar and pestle followed by blending in the desired weight of catalyst. A suitable electrode can be formed by hand coating the well mixed paste directly on a graphite plate of the desired surface area.

In a preferred embodiment, dirhodium complexes are prepared as discussed above. The preferred complex consists of a dirhodium unit bridged by four 2-anilinopyridinate ions and one axially bound chloride ion, $Rh_2(ap)_4Cl$. The ligands are arranged such that the four anilino nitrogens are bound to one rhodium ion and the second rhodium ion contains four equatorial pyridyl nitrogen bonds and one axial chloride bond as shown in FIG. 1.

The carbon paste is prepared by thoroughly mixing 5 g of graphite powder (UPS grade, Ultra Carbon, Inc.) and 3 mL Nujol oil (Aldrich). The dirhodium complex can then be doped into the graphite in a weight/weight ratio of about 2.5%.

Dirhodium(II,II) complex with 2-anilinopyridinate bridging ligand has been shown to reduce molecular oxygen to form a dirhodium(II,III) superoxide complex in aprotic solvents as discussed above. This complex undergoes a one electron reduction at −0.48 V to form a dirhodium(II,II) superoxide complex, $[Rh_2(ap)_4(O_2)]^-$, which reacts with $CH_2Cl_2$ or other superoxide scavengers to reform the original dirhodium(II,II) compound. Therefore, in the presence of dioxygen and at an applied potential of -0.48 V a catalytic cycle for the reduction of dioxygen is established. In aqueous solution the reaction of $[Rh_2(ap)_4(O_2)]^-$ with $H^-$ should facilitate superoxide dissociation in the form of $HO_2$ which disproportionates to form $H_2O_2$ and $O_2$. The complex has an irreversible reduction wave at −0.4 V in this solvent. When one atom $O_2$ is bubbled through the solution, the intensity of the peak current is increased by nine times. The direct reduction of $O_2$ on a pure carbon paste electrode is not seen under the same condition, clearly indicating the electrocatalytical reduction of dioxygen by the dirhodium complex. The net charge flow is presumably due to the final formation of hydrognn peroxide after a reduction of $O_2$.

As can be seen from the foregoing, the present invention provides a unique process and apparatus for catalytically reducing dioxygen using a dirhodium catalyst. While the invention has been described with respect to the presently preferred embodiments, it will be appreciated by those skilled in the art that changes can be made to the invention without departing from its spirit or essential characteristics. For example, the dirhodium complexes of the present invention can be incorporated into other types of electrodes. Accordingly, all modifications or changes which come within the meaning and range of equivalency of the claims are to be embraced within their scope.

What is claimed is:

1. A process for catalytically reducing $O_2$ comprising applying an electric potential to a solution containing $O_2$ and a catalyst comprising a dirhodium complex of the formula $Rh_2(L)_4$ wherein L is a bridging ligand containing two donor atoms selected from the group consisting of N, S, P and O provided that not more than one of the donor atoms in each ligand is O.

2. A process as defined in claim 1 wherein each of the donor atoms is N.

3. A process as defined in claim 2 wherein the ligand comprises a 2-aminopyridinate.

4. A process for catalytically reducing $O_2$ comprising:
   placing tetrakis($\mu$-2-anilinopyridinato)dirhodium in an $O_2$ containing solution; and
   applying an electric potential to said solution.

5. A process for catalytically reducing $O_2$ as defined in claim 4 wherein the tetrakis($\mu$-2-anilinopyridinato)dirhodium is dissolved in the solution.

6. A process for catalytically reducing $O_2$ as defined in claim 4 wherein the tetrakis($\mu$-2-anilinopyridinato)dirhodium is contained in an electrode placed in said solution.

7. A process for catalytically reducing $O_2$ as defined in claim 6 wherein said electrode is a carbon paste electrode.

8. A process for catalytically reducing $O_2$ as defined in claim 4 wherein said electric potential is about −0.48 V.

9. A process for catalytically reducing $O_2$ as defined in claim 4 further comprising adding $O_2$ to the solution.

10. A process for producing hydrogen peroxide comprising:
    placing an electrode comprising tetrakis($\mu$-2-anilinopyridinato)dirhodium in an aqueous solution containing dioxygen; and
    applying an electric potential to said electrode.

11. A process for producing hydrogen peroxide as defined in claim 10 wherein said electric potential is about −0.48 V.

12. A process for producing hydrogen peroxide as defined in claim 10 wherein said electrode is a carbon paste electrode.

13. A process for producing hydrogen peroxide as defined in claim 10 comprising adding oxygen to said solution.

* * * * *